(12) United States Patent
Moretti

(10) Patent No.: US 9,752,096 B2
(45) Date of Patent: Sep. 5, 2017

(54) BI-CYCLO ALDEHYDE AS PERFUMING INGREDIENT

(71) Applicant: FIRMENICH SA, Geneva (CH)

(72) Inventor: Robert Moretti, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/901,398

(22) PCT Filed: Jun. 30, 2014

(86) PCT No.: PCT/EP2014/063789
§ 371 (c)(1),
(2) Date: Dec. 28, 2015

(87) PCT Pub. No.: WO2015/000821
PCT Pub. Date: Jan. 8, 2015

(65) Prior Publication Data
US 2016/0152921 A1    Jun. 2, 2016

(30) Foreign Application Priority Data
Jul. 3, 2013 (EP) ..................................... 13174945

(51) Int. Cl.
| | |
|---|---|
| *A61K 47/00* | (2006.01) |
| *C11B 9/00* | (2006.01) |
| *C07C 47/238* | (2006.01) |
| *A61K 8/33* | (2006.01) |
| *A61Q 13/00* | (2006.01) |
| *C11D 3/00* | (2006.01) |
| *C11D 3/20* | (2006.01) |
| *C11D 3/50* | (2006.01) |
| *A61Q 5/02* | (2006.01) |

(52) U.S. Cl.
CPC ............... *C11B 9/0049* (2013.01); *A61K 8/33* (2013.01); *A61Q 13/00* (2013.01); *C07C 47/238* (2013.01); *C11D 3/001* (2013.01); *C11D 3/2072* (2013.01); *C11D 3/50* (2013.01); *A61Q 5/02* (2013.01)

(58) Field of Classification Search
CPC ......... C11B 9/0049; A61K 8/33; A61Q 13/00; A61Q 5/02; C07C 47/238; C11D 3/001; C11D 3/2072; C11D 3/50
See application file for complete search history.

(56) References Cited

FOREIGN PATENT DOCUMENTS

| | | | | |
|---|---|---|---|---|
| CH | WO 2010052635 A1 | * | 5/2010 | ............. C07C 33/30 |
| WO | WO2010/052635 A1 | | 5/2010 | |

OTHER PUBLICATIONS

International Search Report and Written Opinion, application PCT/EP2014/063789, mailed Sep. 17, 2014.

* cited by examiner

*Primary Examiner* — Jason Sims
*Assistant Examiner* — Ibrahim D Bori
(74) *Attorney, Agent, or Firm* — Winston & Strawn LLP

(57) ABSTRACT

The present invention relates to the field of perfumery and provides certain bi-cyclo derivatives of formula (I)

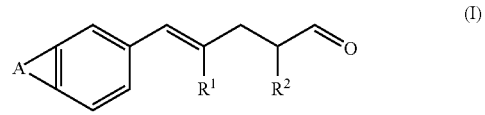

wherein $R^1$ represents a hydrogen atom or a $C_{1-2}$ alkyl group; $R^2$ represents a hydrogen atom or a methyl group; and A represents a group of formula $C_{3-5}$ alkanediyl group; at least one of said $R^1$ or $R^2$ represents a group containing at least one carbon atom. The compounds are in the form of a E or Z isomer or of a mixture thereof. These compounds are valuable perfuming ingredients capable of imparting lily of the valley and citrus notes to consumer products.

20 Claims, No Drawings

BI-CYCLO ALDEHYDE AS PERFUMING INGREDIENT

This application is a 371 filing of International Patent Application PCT/EP2014/063789 filed Jun. 30, 2014, which claims the benefit of European patent application no. 13174945.9 filed Jul. 3, 2013.

TECHNICAL FIELD

The present invention relates to the field of perfumery. More particularly, it concerns some bi-cyclo derivatives of formula (I) and their use as perfuming ingredients to impart lily of the valley and citrus notes. Therefore, following what is mentioned herein, the present invention comprises the invention's compounds as part of a perfuming composition or of a perfuming consumer product.

PRIOR ART

To the best of our knowledge, the compounds of the present invention are novel.

To the best of our knowledge, the closest structural analogues of the present compounds which are reported in the prior art as perfuming ingredients are the ones disclosed in WO2010/052635 and which possess a floral, powdery odor. However, this prior art document does not report or suggest any organoleptic properties of the compounds of formula (I), which have a structure significantly different in the cyclic moiety, or any use of said compounds in the field of perfumery.

DESCRIPTION OF THE INVENTION

We have now surprisingly discovered that a $C_{15}$-$C_{18}$ compound of formula

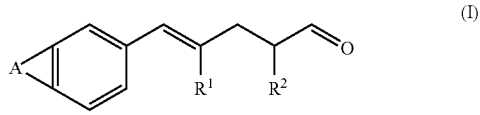

(I)

wherein $R^1$ represents a hydrogen atom or a $C_{1-2}$ alkyl group;
$R^2$ represents a hydrogen atom or a methyl group; and
A represents a group of formula $C_{3-5}$ alkanediyl group;
at least one of said $R^1$ or $R^2$ represents a group containing at least one carbon atom,
and said compound being in the form of a E or Z isomer or of a mixture thereof; can be used as perfuming ingredient, for instance to impart odor notes of the lily of the valley and citrus type.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the double bond is in a conformation E or Z).

According to an embodiment of the invention, said compound (I) is of formula

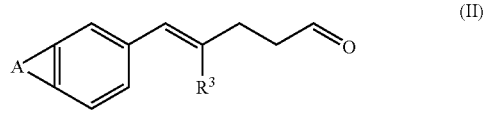

(II)

wherein A has the meaning as indicated above and $R^3$ represents a $C_{1-2}$ alkyl group.

According to any one of the above embodiments of the invention, said compound (I) or (II) is a $C_{15}$ or $C_{17}$ compound.

According to any one of the above embodiments of the invention, said $R^1$ represents a hydrogen atom or a methyl or ethyl group. According to any one of the above embodiments of the invention, said $R^1$ represents a $R^3$ group as defined above in formula (II). According to any one of the above embodiments of the invention, said $R^3$ represents a methyl group.

According to any one of the above embodiments of the invention, said A represents a $C_{3-5}$ alkanediyl group of formula $CH_2CH_2CH_2CH_2$, or $CR_2CR_2CH_2$ wherein each R, independently from each other is a hydrogen atom or a methyl group.

According to any one of the above embodiments of the invention, said A represents a group of formula $CH_2CH_2CH_2CH_2$, $CH_2CH_2C(CH_3)_2$, $CH_2CH_2CH_2$ or $CH_2C(CH_3)HCH_2$.

According to any one of the above embodiments of the invention, said A represents a group of formula $CH_2CH_2CH_2$ or $CH_2CH_2C(CH_3)_2$, and in particular $CH_2CH_2CH_2$.

According to any one of the above embodiments of the invention, said compound can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomers E represent at least 50% of the total mixture, or even at least 75% (i.e. a mixture E/Z comprised between 75/25 and 100/0).

As specific examples of the invention's compounds, one may cite, as non-limiting example, 5-(2,3-dihydro-1H-inden-5-yl)-4-methylpent-4-enal, in the form of a E/Z=85/15 mixture, which possesses an odor characterized by a lily of the valley, aldehyde and citrusy note having also the typical "wetness" of 3-(4-tert-butylphenyl)-2-methylpropanal (a well know perfuming ingredient known as Lilial® from Givaudan SA). Its performance reminds strongly the one of the well known perfuming ingredient 3-(4-tert-butylphenyl)-2-methylpropanal without having anisic aspects, which can be present in prior art compounds.

As other example, one may cite 5-(2,3-dihydro-1H-inden-5-yl)-4-methylpent-4(E)-enal, which possesses an odor similar to the one mentioned above but distinguishing itself by having a stronger note.

As other specific, but non-limiting, examples of the invention's compounds, one may cite the following ones in Table 1:

TABLE 1

Invention's compounds and their odor properties

| Compound structure and name | Odor notes |
|---|---|
|  | Odor similar to the one of 5-(2,3-dihydro-1H-inden-5-yl)-4-methylpent-4-enal, although weaker |
| 80/20 mixture of (E)/(Z)-4-methyl-5-(5,6,7,8-tetrahydronaphthalen-2-yl)pent-4-enal | |

TABLE 1-continued

Invention's compounds and their odor properties

| Compound structure and name | Odor notes |
|---|---|
| 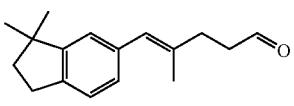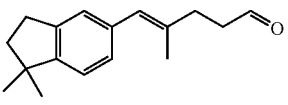50/50 mixture of (E)-5-(3,3/1,1-dimethyl-2,3-dihydro-1H-inden-5-yl)-4-methylpent-4-enal | Odor similar to the one of 5-(2,3-dihydro-1H-inden-5-yl)-4-methylpent-4-enal, although having a green and aldehydic aspect |

According to a particular embodiment of the invention, the compound of formula (I) is 5-(2,3-dihydro-1H-inden-5-yl)-4-methylpent-4-enal.

When the odor of the invention's compounds is compared with that of the prior art compounds disclosed in WO2010/052635, then the invention's compounds distinguish themselves by lacking a, or not possessing a significant anisic/powdery duality, as well as by having a citrus note. Said differences lend the invention's compounds and the prior art compounds to be each suitable for different uses, i.e. to impart different organoleptic impressions.

These differences with the compounds of WO2010/052635 are quite surprising since indeed all the compounds cited in WO2010/052635 which are devoid of the anisic duality are the ones wherein either the aromatic ring is not substituted or have a methyl substituent in the benzylic position of the aldehyde chain and are C12-14 compounds, so significantly different in their structure.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a to compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
  i) as perfuming ingredient, at least one invention's compound as defined above;
  ii) at least one ingredient selected from the group consisting of a perfumery carrier and a perfumery base; and
  iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, another object of the present invention is represented by a perfuming consumer product comprising, as perfuming ingredient, at least one compound of formula (I), as defined above.

The invention's compound can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's compound.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.1% to 30% by weight, or even more, of the compounds of the invention based on the weight of the composition into which they are incorporated. Concentrations lower than these, such as in the order of 1% to 10% by weight, can be used when these compounds are incorporated into perfumed articles, percentage being relative to the weight of the article.

The invention's compounds can be obtained by a process comprising the following key steps:

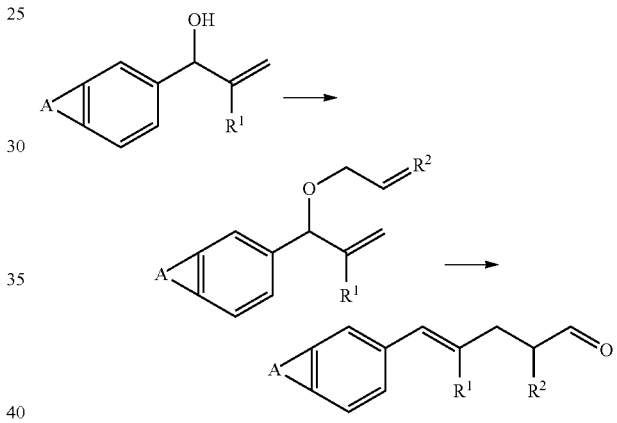

Examples of all said methodologies are provided herein below in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Preparation of
2,3-dihydro-1H-indene-5-carbaldehyde

Indane (15 g; 127 mmol) was dissolved under nitrogen in dry dichloromethane (150 ml) and the solution cooled at −30° C. Tin tetrachloride (50 g; 190 mmol, 1.5 eq.) was added all at once, followed by the dropwise addition of dichloromethyl methyl ether (11.6 g; 127 mmol). The cooling bath was removed after 20 minutes. After the reaction had reached room temperature, it was cooled to 0° C. and quenched by the addition of ice-water (100 ml). The reaction was extracted with diethyl ether (2×250 ml). Each extract was washed with water (2×100 ml), 5% aqueous HCl (50 ml) and brine (2×100 ml). Combined extracts were dried over sodium sulfate. The product was purified by column chromatography on silica gel (heptane/ethyl acetate 98:2) followed by bulb-to-bulb distillation (80° C./0.005 mbar).

The product was obtained as a liquid (9.8 g; purity 97%; yield: 51%).

$^{13}$C-NMR: 192.22 (d); 152.01 (s); 145.26 (s); 135.29 (s); 128.86 (d); 125.15 (d); 124.79 (d); 33.17 (t); 32.37 (t); 25.34 (t).

$^1$H-NMR: 9.93 (s, 1H); 7.72 (s, 1H); 7.64 (m, 1H); 7.34 (m, 1H); 2.95 (t, J=7 Hz; 4H); 2.12 (quintuplet; J=7 Hz; 2H).

Preparation of 1-(2,3-dihydro-1H-inden-5-yl)-2-methylprop-2-en-1-ol

Lithium (containing 1% sodium; 1.16 g; 168 mmol; 2.5 eq.) was covered with dry diethyl ether (30 ml) under nitrogen. After cooling to −30° C., 2-bromopropene (10.14 g; 84 mmol; 1.25 eq) in dry diethyl ether (50 ml) was added over 45 minutes. After 3 more hours at −30° C., the reaction was cooled to −78° C. and 2,3-dihydro-1H-indene-5-carb-aldehyde (9.8 g; 67 mmol) in dry diethyl ether (70 ml) was added dropwise over 60 minutes. After 90 more minutes, the reaction was poured onto aqueous saturated NH$_4$Cl. The mixture was extracted twice with diethyl ether. Each aqueous phase was washed with water and brine. Combined extracts were dried over sodium sulfate. The product was purified by column chromatography on silica gel (heptane/ethyl acetate 5:1) followed by bulb-to-bulb distillation (140° C./0.05 mbar).

The product was obtained as a liquid (purity: 97%; 54 mmol; 81%).

$^{13}$C-NMR: 147.05 (s); 144.49 (s); 143.76 (s); 140.03 (s); 124.56 (d); 124.18 (d); 122.46 (d); 110.57 (t); 77.88 (d); 32.79 (t); 32.56 (t); 25.50 (t); 18.54 (q).

$^1$H-NMR: 7.22-7.08 (m, 3H); 5.20 (s, 1H); 5.04 (s; 1H); 4.92 (s; 1H); 2.90 (t, J=7 Hz; 4H); 2.06 (quintuplet, J=7 Hz, 2H); 2.05 (broad s, 1H); 1.62 (s, 3H).

Synthesis of Compounds of Formula (I)

1. Preparation of 5-(2,3-dihydro-1H-inden-5-yl)-4-methylpent-4-enal, in the form of a E/Z=85/15 Mixture 3,6,9,12-tetraoxatetradeca-1,13-diene (50 g; 242 mmol), mercuric acetate (3.8 g; 12 mmol) and 1-(2,3-dihydro-1H-inden-5-yl)-2-methylprop-2-en-1-ol (40 g; 202 mmol) were stirred and heated together to 100-105° C. overnight. After cooling to 60° C., a solution containing AcOH/water/sodium acetate 64/18/18 (80 ml) was added and the mixture was heated to 120° C. under nitrogen (bath temp.) for 1.5 hours. After cooling to room temperature, diethyl ether (500 ml) was added. The mixture was washed with water (2×1.5 liter); aqueous saturated NaHCO$_3$ (1 liter) and brine (500 ml). Each aqueous phase was reextracted with diethyl ether (500 ml). Combined extracts were dried over sodium sulfate. The product was purified by column chromatography on silica gel (heptane/ethyl acetate 15:1 to 5:1) followed by bulb-to-bulb distillation (120-130° C./0.014 mbar).

The product was obtained as a 85:15 E/Z isomer mixture (20.5 g; yield: 47%).

$^{13}$C-NMR (major isomer): 202.12 (d); 144.07 (s); 142.19 (s); 135.90 (s); 135.66 (s); 126.79 (d); 126.12 (d); 124.69 (d); 123.92 (d); 42.26 (t); 32.83 (t); 32.77 (t); 32.59 (t); 25.46 (t); 17.85 (q).

$^1$H-NMR: 9.80 (t, J=1.8 Hz; 1H); 7.18-6.90 (m, 3H); 6.27 (s, 1H); 2.88 (m, 4H); 2.64-2.59 (m, 4H); 2.05 (quintuplet; J=7 Hz, 2H); 1.82 (s; 3H).

2. Preparation of 5-(2,3-dihydro-1H-inden-5-yl)-4-methylpent-4(E)-enal a) (E)-ethyl 5-(2,3-dihydro-1-inden-5-yl)-4-methyl-pent-4-enoate 1-(2,3-Dihydro-1H-inden-5-yl)-2-methylprop-2-en-1-ol (10 g, 53 mmol), 2-ethylhexanoic acid (0.21 g 1.6 mmol; 0.03 eq)) and triethylorthoacetate (22 g; 133 mmol, 2.5 eq) were dissolved in toluene (20 ml). The solution was heated in a stainless steel autoclave (purged with nitrogen) to 180° C. overnight. After cooling to room temperature, the reaction was concentrated on the rotavapor. The product was purified by column chromatography on silica gel (heptane/ethyl acetate 9:1) followed by bulb-to-bulb distillation (95° C./0.05 mbar).

The product was obtained as a liquid (11.4 g; purity: 92%; yield: 76%).

$^{13}$C-NMR: 173.25 (s); 144.04 (s); 142.07 (s); 136.14 (s); 136.03 (s); 126.82 (d); 125.94 (d); 124.71 (d); 123.90 (d); 60.33 (t); 35.72 (t); 33.28 (t); 32.84 (t); 32.60 (t); 25.48 (t); 17.69 (q); 14.29 (q).

$^1$H-NMR: 7.18-6.96 (m, 3H); 6.28 (broad s, 1H); 4.14 (q, J=7 Hz; 2H); 2.88 (m, 4H); 2.54-2.45 (m, 4H); 2.06 (quintuplet; J=7 Hz; 2H); 1.86 (d, J=1.3 Hz; 3H); 1.25 (t, J=7 Hz, 3H).

b) (E)-5-(2,3-dihydro-1-inden-5-yl)-4-methylpent-4-en-1-ol (E)-ethyl 5-(2,3-dihydro-1H-inden-5-yl)-4-methylpent-4-enoate (11.4 g; 44 mmol) in dry diethyl ether (100 ml) was slowly added to a slurry of lithium aluminum hydride (1.93 g; 48.5 mmol) in dry diethyl ether (50 ml). After 1 hour, the reaction was cooled to 0-5° C. and water (2 ml), 5% aqueous NaOH (6 ml) and again water (2 ml) were successively and very cautiously added to the reaction. The cooling bath was removed and the reaction stirred until a slurry was obtained. The reaction medium was dried over sodium sulfate. The solid was filtered, thoroughly rinsed with diethyl ether. The filtrate was concentrated on the rotavapor. The product was purified by bulb-to-bulb distillation (95° C./0.02 mbar).

The product was obtained a liquid (7 g; purity: 98%; yield: 72%).

$^{13}$C-NMR: 144.04 (s); 141.93 (s); 137.47 (s); 136.33 (s); 126.79 (d); 125.51 (d); 124.68 (d); 123.90 (d); 62.66 (t); 36.99 (t); 32.84 (t); 32.59 (t); 30.92 (t); 25.48 (t); 17.76 (q).

$^1$H-NMR: 7.18-6.98 (m, 3H); 6.28 (broad s, 1H); 3.68 (broad t, J=6.5 Hz, 2H); 2.88 (m, 4H); 2.24 (m, 2H); 2.06 (quintuplet, J=7 Hz, 2H); 1.87 (d, J=1.3 Hz, 3H); 1.81-1.75 (m, 2H); 1.67 (broad s, 1H).

c) 5-(2,3-dihydro-1H-inden-5-yl)-4-methylpent-4 (E)-enal

PCC (5.34 g; 24.3 mmol) was added portionwise to a mixture of the above prepared alcohol (3.5 g; 16.2 mmol) in dry dichloromethane (70 ml) and celite (10 g), at 0° C. under nitrogen. The reaction was then warmed up to room temperature. The reaction was filtered through silica gel, rinsing with diethyl ether. The filtrate was concentrated under vacuum. The product was purified by column chromatography on silica gel (heptane/ethyl acetate 9:1) followed by bulb-to-bulb distillation (100° C./0.05 mbar).

The product was obtained as a liquid (1.7 g; purity: 95%; yield: 47%). Analysis shows it is essentially the E-isomer.

$^{13}$C-NMR: 202.13 (d); 144.08 (s); 142.20 (s); 135.90 (s); 135.66 (s); 126.79 (d); 126.12 (d); 124.70 (d); 123.93 (d); 42.26 (t); 32.83 (t); 32.77 (t); 32.59 (t); 25.47 (t); 17.85 (q).

$^{1}$H-NMR: 9.80 (t, J=1.8 Hz; 1H); 7.18-6.90 (m, 3H); 6.27 (s, 1H); 2.88 (m, 4H); 2.64-2.59 (m, 4H); 2.05 (quintuplet; J=7 Hz, 2H); 1.82 (s; 3H).

3. Preparation of 4-methyl-5-(5,6,7,8-tetrahydronaphthalen-2-yl)pent-4-enal, in the form of a E/Z=80/20 Mixture a) Preparation of 5,6,7,8-tetrahydronaphthalene-2-carbaldehyde 1,2,3,4-tetrahydronaphthalene (14.5 g; 110 mmol) was dissolved in dry of $CH_2Cl_2$ (100 ml) and the solution cooled to 0° C. on an ice bath. With vigorous stiffing, $SnCl_4$ (33.4 g; 164 mmol) was add all at once via syringe, followed by the dropwise introduction of dichloromethyl methyl ether (12.6 g; 110 mmol) over a 20 minutes period. After 20 more minutes the ice bath was removed, and the dark mixture was quenched by the addition of 100 ml of ice-water. The reaction was extracted with diethyl ether (2×250 ml). Each extract was washed with water (2×100 ml), 5% aqueous HCl (50 ml) and brine (2×100 ml). Combined extracts were dried over sodium sulfate. The product was purified by column chromatography on silica gel (heptane/ethyl acetate 98:2) followed by bulb-to-bulb distillation (85° C./0.002 mbar).

The product was obtained as a liquid (40.5 mmol; yield: 44%)

$^{13}$C-NMR (major isomer): 192.28 (d); 144.86 (s); 138.01 (s); 134.24 (s); 130.80 (d); 129.81 (d); 126.59 (d); 29.93 (t); 29.23 (t); 22.84 (t); 22.72 (t).

$^{1}$H-NMR: 9.91 (s, 1H); 7.60-7.50 (m, 2H); 7.19 (d, J=7.5 Hz, 1H); 2.82 (m, 4H); 1.81 (m, 4H).

b) Preparation of 2-methyl-1-(5,6,7,8-tetrahydronaphthalen-2-yl)prop-2-en-1-ol Lithium (containing 1% sodium; 0.68 g; 98 mmol) was covered with dry diethyl ether (30 ml) under Argon. After cooling to −30° C., 2-bromopropene (5.95 g; 49 mmol) in dry diethyl ether (50 ml) was added over 45 minutes. After two more hours at −30° C., the reaction was cooled to −78° C., the above prepared aldehyde (6.3 g; 39 mmol) in dry diethyl ether (70 ml) was added over 1 hour. After stirring to −7° C. for 90 more minutes, the reaction was poured onto water and extracted twice with diethyl ether. The organic phases were washed with brine and dried over sodium sulfate. The product was purified by column chromatography on silica gel (heptane/ethyl acetate 5:1) followed by bulb-to-bulb distillation (140° C./0.05 mbar). The product was obtained as a liquid (6 g; 30 mmol; yield: 60%).

$^{13}$C-NMR (major isomer): 146.91 (s); 139.13 (s); 137.16 (s); 136.63 (s); 129.16 (d); 127.14 (d); 123.65 (d); 110.69 (t); 77.73 (d); 29.45 (t); 29.16 (t); 23.26 (t); 23.21 (t); 18.51 (q).

$^{1}$H-NMR: 7.10 (m, 3H); 5.20 (s, 1H); 5.03 (d, J=3.3 Hz; 1H); 4.93 (s, 1H); 2.75 (m, 4H); 1.96 (d, J=3.5 Hz, 1H); 1.78 (m, 4H); 1.61 (s, 3H).

c) Preparation of 4-methyl-5-(5,6,7,8-tetrahydronaphthalen-2-yl)pent-4-enal The above prepared alcohol (5 g; 24 mmol), mercuric acetate (0.46 g; 1.4 mmol) and 3,6,9,12-tetraoxatetradeca-1,13-diene (5.94 g; 29 mmol) were heated together under nitrogen at 110° C. overnight. After cooling to room temperature, the reaction was directly chomatographed on silica gel (heptane/ethyl acetate 98:2 to 90:10). The product was further purified by bulb-to-bulb distillation (160° C./0.03 mbar).

The product was obtained as a liquid and in the form of a 80:20 E/Z mixture (1.8 g; yield: 33%).

$^{13}$C-NMR (major isomer): 202.13 (d); 136.73 (s); 135.75 (s); 135.17 (s); 135.12 (s);
129.44 (d); 128.80 (d); 125.97 (d); 125.80 (d); 42.26 (t); 32.77 (t); 29.44 (t); 29.11 (t); 23.26 (t); 23.25 (t); 17.85 (q).

$^{1}$H-NMR: 9.80 (t, J=1.8 Hz, 1H); 7.05-6.84 (m, 3H); 6.23 (broad s, 1H); 2.75 (m, 4H); 2.65-2.45 (m, 4H); 1.86 (d, J=1.3 Hz, 3H); 1.78 (m, 4H).

4. Preparation of 4-methyl-5-(5,6,7,8-tetrahydronaphthalen-2-yl)pent-4-enal, in the form of a E/Z=50/50 Mixture a) Preparation of (3,3/1,1)-dimethyl-2,3-dihydro-1H-indene-5-carbaldehyde 1,1-dimethyl-2,3-dihydro-1H-indene (20 g, 137 mmol) was dissolved in dry $CH_2Cl_2$ (150 ml) and the solution was cooled to −30° C. With vigorous stiffing, $SnCl_4$ (54 g; 205 mmol) was added all at once via syringe, followed by the dropwise introduction of dichloromethyl methyl ether (15.72 g; 137 mmol) over a 30 minutes period. After 20 minutes, the ice bath was removed. Upon reaching room temperature, the reaction was cooled to 0° C. and the dark mixture was quenched by the addition of 100 ml of ice-water.

The reaction mixture was extracted twice with diethyl ether. Each organic phase was successively washed with water (twice), 5% aqueous HCl and brine (twice). The combined organic phases were dried over sodium sulfate.

The product was purified by column chromatography on silica gel (heptane/ethyl acetate 98:2) followed by bulb-to-bulb distillation (90° C./0.02 mbar).

The product was obtained as a liquid and in the form of a 1/1 mixture of regioisomers (1,1)/(3,3) (purity: 96%; 12.9 g; yield: 52%).

$^{13}$C-NMR: 192.27 (d); 192.19 (d); 160.12 (s); 153.78 (s); 150.73 (s); 143.88 (s); 135.65 (s); 135.40 (s); 129.39 (d); 129.32 (d); 125.50 (d); 125.01 (d); 122.66 (d); 122.50 (d); 44.29 (s); 43.76 (s); 41.23 (t); 41.21 (t); 30.42 (t); 29.63 (t); 28.47 (q); 28.23 (q).

$^{1}$H-NMR: 9.97 (s, 0.5H); 9.95 (s, 0.5H); 7.71-7.63 (m, 2H); 7.37-7.25 (m, 1H); 2.95 (m, 2H); 1.98 (t, J=7 Hz, 2H); 1.29 (s, 3H); 1.28 (s, 3H).

b) Preparation of 1-(3,3/1,1)-dimethyl-2,3-dihydro-1H-inden-5-yl)-2-methylprop-2-en-1-ol The above prepared aldehyde (12.9 g; 74 mmol) was added over 1 hour to the Grignard reagent solution (0.5 M in THF; 178 ml; 89 mmol), at −78° C. under nitrogen. At the end of the addition, the cooling bath was removed and the reaction stirred for 2 hours. The reaction was cooled into an ice-ethanol bath and aqueous saturated $NH_4Cl$ (200 ml) was added slowly. The mixture was warmed up to room temperature, and the phases were separated. The organic phase was washed with brine (150 ml). Each aqueous phase was re-extracted with diethyl ether (200 ml). Combined org. phases were dried over sodium sulfate. The product was purified by bulb-to-bulb distillation (100-110° C./0.01 mbar).

The product was obtained as a liquid in the form of a 1/1 mixture of regioisomers (14.1 g; purity: 98%; yield: 86%).

$^{13}$C-NMR: 152.85 (s); 152.21 (s); 147.05 (s); 147.00 (s); 143.05 (s); 142.35 (s); 140.33 (s); 140.08 (s); 124.88 (d); 124.65 (d); 124.30 (d); 122.56 (d); 121.82 (d); 120.14 (d); 110.75 (t); 110.55 (t); 78.06 (d); 77.92 (d); 43.90 (t); 43.69 (t); 41.57 (t); 41.52 (t); 29.98 (t); 29.76 (t); 28.59 (q); 28.58 (q); 18.61 (q); 18.50 (q).

1H-NMR: 7.23-7.05 (m, 3H); 5.21-4.92 (m, 3H); 2.86 (t, J=7 Hz, 2H); 1.91 (m, 3H); 1.62 (m, 3H); 1.25 (s, 3.6H); 1.24 (s, 2.4H).

c) Preparation of ethyl 5-((3,3/1,1)-dimethyl-2,3-dihydro-1H-inden-5-yl)-4-methylpent-4-enoate The above prepared alcohol (1:1 regioisomer mixture, 8.7 g; 40.2 mmol); triethylorthoacetate (16.64 g; 101 mmol) and 2-ethylhexanoic acid (0.16 g; 1.2 mmol) in toluene (20 ml) were heated in a stainless steel autoclave (purged with nitrogen) at 160° C. for 2 hours, then 180° C. for 4 hours. After cooling to room temperature, the reaction was concentrated in vacuum. The product was purified by column chromatography on silica gel (heptane/ethyl acetate 9:1) followed by bulb-to-bulb distillation (95° C./0.01 mbar).

The product was obtained as 1:1 mixture of regioisomers (8.7 g; yield: 64%).

$^{13}$C-NMR: 173.30 (s); 173.27 (s); 152.38 (s); 150.53 (s); 142.63 (s); 140.71 (s); 136.40 (s); 136.27 (s); 136.01 (s); 135.99 (s); 127.15 (d); 126.90 (d); 126.09 (d); 125.92 (d); 124.79 (d); 124.79 (d); 124.00 (d); 122.45 (d); 121.53 (d); 60.34 (t); 43.84 (s); 43.72 (s); 41.54 (t); 41.49 (t); 35.75 (t); 35.72 (t); 33.30 (t); 33.28 (t); 30.02 (t); 29.78 (t); 28.59 (q); 17.75 (q); 17.72 (q); 14.29 (q).

$^{1}$H-NMR: 7.20-6.82 (m, 3H); 6.30 (broad s, 0.5H); 6.27 (broad s, 0.5H); 4.15 (m, 2H); 2.83 (m, 2H); 2.50 (m, 4H); 1.91 (m, 2H); 1.87 (s, 3H); 1.28-1.22 (m, 3H); 1.25 (s, 6H).

d) Preparation of ethyl 5-((3,3/1,1)-dimethyl-2,3-dihydro-1H-inden-5-yl)-4-methylpent-4-enoate The above prepared ester (8.7 g; 84% pure by GC; 25.5 mmol) in dry diethyl ether (100 ml) was added dropwise to a slurry of lithium aluminum hydride (1.34 g; 33.4 mmol). After 1 hour, the reaction was cooled into an ice/water bath and treated successively (and cautiously) with water (2 ml), 5% aqueous NaOH (6 ml) and water (2 ml). After warming up to room temperature, a slurry was obtained. It was dried by addition of sodium sulfate. The solid was filtered off, thoroughly rinsed with diethyl ether. The filtrate was concentrated in vacuum. The product was purified by bulb-to-bulb distillation (95° C./0.02 mbar). The product was obtained as a 1:1 mixture of regioisomers (4.9 g; purity: 96%; yield: 75%).

$^{13}$C-NMR: 152.38 (s); 150.40 (s); 142.64 (s); 140.58 (s); 137.43 (s); 137.41 (s); 136.59 (s); 136.46 (s); 127.12 (d); 126.87 (d); 125.71 (d); 125.53 (d); 124.76 (d); 124.00 (d); 122.42 (d); 121.54 (d); 62.71 (t); 62.68 (t); 43.84 (t); 43.70 (t); 41.54 (t); 41.49 (t); 37.05 (t); 37.00 (t); 30.92 (t); 30.02 (t); 29.77 (t); 28.59 (q); 17.81 (q); 17.79 (q).

$^{1}$H-NMR: 7.13-6.99 (m, 3H); 6.31 (m, 0.5H); 6.28 (m, 0.5H); 3.70 (m, 2H); 2.86 (m, 2H); 2.25 (m, 2H); 1.92 (m, 2H); 1.88 (broad s, 3H); 1.79 (m, 2H); 1.25 (s, 6H).

e) Preparation of 4-methyl-5-(5,6,7,8-tetrahydronaphthalen-2-yl)pent-4-enal

A mixture of the above obtained alcohol (4.9 g; 19.2 mmol) and celite (20 g) in dry dichloromethane (150 ml) was cooled into an ice/water bath and treated portionwise with PCC (6.62 g; 30 mmol). The reaction was warmed up to room temperature. The mixture was filtered through silica gel, rinsing with diethyl ether. The filtrate was concentrated in vacuum. The product was purified by column chromatography on silica gel (heptane/ethyl acetate 9:1) followed by bulb-to-bulb distillation (100° C./0.05 mbar).

The product was obtained as a 1:1 mixture of regioisomers (purity: 95%; 2.4 g; yield: 49%).

$^{13}$C-NMR: 202.18 (d); 202.16 (d); 152.44 (s); 150.67 (s); 142.69 (s); 140.85 (s); 136.17 (s); 136.03 (s); 135.63 (s); 135.61 (s); 127.14 (d); 126.88 (d); 126.30 (d); 126.14 (d); 124.79 (d); 124.05 (d); 122.45 (d); 121.58 (d); 43.85 (t); 43.73 (t); 42.30 (t); 42.28 (t); 41.53 (t); 41.48 (t); 32.85 (t); 32.78 (t); 30.01 (t); 29.79 (t); 28.72 (q); 28.59 (q); 17.91 (q).

$^{1}$H-NMR: 9.82 (m, 1H); 7.15-6.97 (m, 3H); 6.30 (m, 0.5H); 6.28 (m, 0.5H); 2.86 (m, 2H); 2.64 (m, 2H); 2.50 (m, 2H); 1.92 (m, 2H); 1.87 (broad s, 3H); 1.25 (s, 6H).

Example 2

Preparation of a Perfuming Composition

A perfuming composition for a shampoo, of the floral, green type, was prepared by admixing the following ingredients:

| Parts by weight | Ingredient |
| --- | --- |
| 150 | Benzyl acetate |
| 150 | Geranyl acetate |
| 200 | Neryl acetate |
| 10 | Prenyl acetate |
| 20 | Styrallyl acetate |
| 50 | Hexyl acetate |
| 20 | Aladinate ® [1] |
| 50 | 10%* Aldehyde C 11 Lenique |
| 400 | Hexylcinnamic aldehyde |
| 20 | Allyl amyl glycolate |
| 40 | Ethyl 2-methyl-pentanoate |
| 50 | Cetalox ® [2] |
| 50 | 10%* Cis-3-hexenol |
| 120 | Coranol ™ [3] |
| 60 | Allyl (cyclohexyloxy)-acetate |
| 40 | 10%* Damascenone |
| 50 | 1-(2,6,6-trimethyl-1-cyclohexen-2-yl)-2-buten-1-one |
| 50 | 10%* 1-(2,6,6-trimethyl-1-cyclohexen-1-yl)-2-buten-1-one |
| 50 | 10%* Ethyl 2-methylbutyrate |
| 100 | Florol ® [4] |
| 80 | Decalactone gamma |
| 450 | Habanolide ® [5] |
| 500 | Hedione ® [6] |
| 50 | Helvetolide ® [7] |
| 100 | Iso E ® [8] Super |
| 10 | Jasminlactone |
| 800 | Linalool |
| 200 | Lyral ® [9] |
| 20 | Crystal moss oil |
| 50 | Muscenone ™ [10] Delta |
| 10 | 10%* Neobutenone ® [11] |
| 150 | Phenylhexanol |
| 300 | Romandolide ® [12] |
| 150 | Benzyl salicylate |

-continued

| Parts by weight | Ingredient |
|---|---|
| 100 | Cis-3-hexenol salicylate |
| 250 | Terpineol |
| 30 | 2,4-Dimethyl-3-cyclohexene-1-carbaldehyde |
| 20 | Undecalactone gamma |
| 50 | Verdox ® 13) |
| 5000 | |

*in dipropyleneglycol
1) 3-methyl-2-hexenyl acetate; origin: Firmenich SA, Geneva, Switzerland
2) dodecahydro-3a,6,6,9a-tetramethyl-naphtho[2,1-b]furan; origin: Firmenich SA, Geneva, Switzerland
3) 4-cyclohexyl-2-methyl-2-butanol; origin: Firmenich SA, Geneva, Switzerland
4) tetrahydro-2-isobutyl-4-methyl-4(2H)-pyranol; origin: Firmenich SA, Geneva, Switzerland
5) pentadecenolide; origin: Firmenich SA, Geneva, Switzerland
6) methyl dihydrojasmonate; origin: Firmenich SA, Geneva, Switzerland
7) (1S,1'R)-2-[1-(3',3'-dimethyl-1'-cyclohexyl)ethoxy]-2-methylpropyl propanoate; origin: Firmenich SA, Geneva, Switzerland
8) 1-(octahydro-2,3,8,8-tetramethyl-2-naphthalenyl)-1-ethanone; origin: International Flavors & Fragrances, USA
9) 4/3-(4-hydroxy-4-methylpentyl)-3-cyclohexene-1-carbaldehyde; origin: International Flavors & Fragrances, USA
10) 3-methyl-5-cyclopentadecen-1-one; origin: Firmenich SA, Geneva, Switzerland
11) 1-(5,5-dimethyl-1-cyclohexen-1-yl)-4-penten-1-one; origin: Firmenich SA, Geneva, Switzerland
12) (1S,1'R)-[1-(3',3'-dimethyl-1'-cyclohexyl)ethoxycarbonyl]methyl propanoate; origin: Firmenich SA, Geneva, Switzerland
13) 2-tert-butyl-1-cyclohexyl acetate; origin: International Flavors & Fragrances, USA The addition of 1000 parts by weight of 5-(2,3-dihydro-1H-inden-5-yl)-4-methylpent-4-enal, as obtained in Example 1.1), to the above-described composition imparted to the latter a sweet and warm lily of the valley connotation. The effect was very close to the one obtained by the addition of 3-(4-tert-butylphenyl)-2-methylpropanal instead of the invention's compound.

Example 3

Preparation of a Perfuming Composition

A perfuming composition for a softener, of the floral, oriental type, was prepared by admixing the following ingredients:

| Parts by weight | Ingredient |
|---|---|
| 100 | Benzyl acetate |
| 10 | Anisic aldehyde |
| 60 | Aldehyde C 11 Lenique |
| 200 | Benzyl benzoate |
| 40 | Cetalox ® 1) |
| 30 | Raspberry ketone |
| 80 | Coranol ™ 1) |
| 70 | Coumarine |
| 10 | Allyl cyclohexylpropionate |
| 40 | 10%* Methyl cyclopentylideneacetate |
| 20 | Damascone Alpha |
| 50 | Ethylvanilline |
| 300 | Eugenol |
| 20 | 10%* Florex ® 2) |
| 10 | Geraniol formiate |
| 50 | 10%* Gamma jasmolactone |
| 100 | Geraniol |
| 400 | Habanolide ® 1) |
| 300 | Hedione ® 1) |
| 20 | 1,3-Benzodioxole-5-carbaldehyde |
| 100 | Helvetolide ® 1) |
| 20 | Hivernal ® 3) |
| 40 | Isoeugenol |
| 10 | Isopentyrate |
| 500 | Methyl alpha ionone |
| 20 | 10%* Menthone |
| 60 | Methyl nonyl acetaldehyde |
| 40 | Methylnaphthylcetone |
| 60 | Methylparacresol |

| Parts by weight | Ingredient |
|---|---|
| 30 | Crystal moss oil |
| 100 | Muscenone ® 1) Delta |
| 10 | Myroxyde ® 4) |
| 30 | 10%* Neobutenone ® 1) |
| 20 | Rose oxide |
| 300 | Patchouli oil |
| 50 | 0.1%* (2E,6Z)-2,6-nonadienal |
| 100 | Phenylhexanol |
| 20 | Benzyl propionate |
| 20 | Phenylethyl salicylate |
| 140 | Salicynile ® 5) |
| 20 | Terpineol |
| 10 | 2-Ethyl-4,4-dimethyl-1-cyclohexanone |
| 10 | 3-Phenylbutanal |
| 20 | 2,4-Dimethyl-3-cyclohexene-1-carbaldehyde |
| 50 | Undecalactone gamma |
| 20 | Veloutone ™ 6) |
| 250 | Methyl cedryl ketone |
| 40 | 10%** Z 11 7) |
| 4000 | |

*in dipropyleneglycol
**in isopropyle myristate
1) see above example 2
2) 9/10-ethylidene-3-oxatricyclo[6.2.1.0(2,7)]undecan-4-one; origin: Firmenich SA, Geneva, Switzerland
3) 3-(3,3/1,1-dimethyl-5-indanyl)propanal; origin: Firmenich SA, Geneva, Switzerland
4) 6,7-epoxy-3,7-dimethyl-1,3-octadiene; origin: Firmenich SA, Geneva, Switzerland
5) (2Z)-2-phenyl-2-hexenenitrile; origin: Firmenich SA, Geneva, Switzerland
6) 2,2,5-trimethyl-5-pentyl-1-cyclopentanone; origin: Firmenich SA, Geneva, Switzerland
7) (1S,4S,9S,10R,13R)-5,5,9,13-tetramethyl-14,16-dioxatetracyclo[11.2.1.0 (1,10).0(4,9)]hexadecane; origin: Firmenich SA, Geneva, Switzerland The addition of 1000 parts by weight of 5-(2,3-dihydro-1H-inden-5-yl)-4-methylpent-4-enal, as obtained in Example 1.1), to the above-described composition imparted to the latter a nice green, lily of the valley twist, with a cosmetic effect and softening the Patchouli note. The effect was once again close to the one obtained by the addition of 3-(4-tert-butylphenyl)-2-methylpropanal instead of the invention's compound.

What is claimed is:
1. A compound of formula

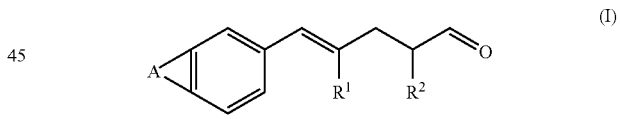

(I)

wherein $R^1$ represents a hydrogen atom or a $C_{1-2}$ alkyl group;
$R^2$ represents a hydrogen atom or a methyl group;
A represents a group of formula $C_{3-5}$ alkanediyl group; and
at least one of said $R^1$ or $R^2$ represents a group containing at least one carbon atom, said compound being in the form of a E or Z isomer or of a mixture thereof.
2. A compound according to claim 1, which is of formula

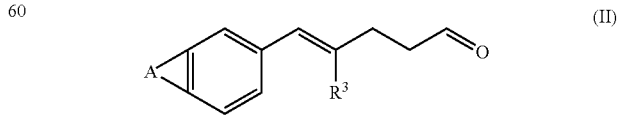

(II)

wherein A has the meaning as defined in claim 1 and $R^3$ represents a $C_{1-2}$ alkyl group.

3. A compound according to claim 1, wherein $R^1$ represents a hydrogen atom or a methyl or ethyl group.

4. A compound according to claim 1 wherein A represents a $C_{3-5}$ alkanediyl group of formula $CH_2CH_2CH_2CH_2$, or $CR_2CR_2CH_2$ wherein each R, independently from each other is a hydrogen atom or a methyl group.

5. A compound according to claim 4, wherein A represents a group of formula $CH_2CH_2CH_2$ or $CH_2CH_2C(CH_3)_2$.

6. A compound according to claim 1, which is in the form of mixture consisting of isomers E and Z and wherein said isomers E represent at least 50% of the total mixture.

7. A compound according to claim 1, which is 5-(2,3-dihydro-1H-inden-5-yl)-4-methylpent-4-enal.

8. A perfuming composition comprising
   i) at least one compound of formula (I), as defined in claim 1;
   ii) at least one ingredient selected from the group consisting of a perfumery carrier and a perfumery base; and
   iii) optionally at least one perfumery adjuvant.

9. A perfuming consumer product comprising at least one compound of formula (I), as defined in claim 1.

10. A perfuming consumer product according to claim 9, wherein the perfumery consumer product is a perfume, a fabric care product, a body-care product, an air care product or a home care product.

11. A perfuming consumer product according to claim 9, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

12. A method to impart or modify odor notes of the lily of the valley and citrus types of a consumer product which comprises including in the product a perfuming ingredient comprising the compound (I) of claim 1.

13. A compound according to claim 1 in a mixture with:
   at least one ingredient selected from the group consisting of a perfumery carrier and a perfumery base; and
   optionally at least one perfumery adjuvant.

14. A compound according to claim 1 which is present in a perfuming consumer product.

15. A perfuming consumer product according to claim 9, wherein the perfumery consumer product is a perfume, a fabric care product, a body-care product, an air care product or a home care product.

16. A perfuming consumer product according to claim 9, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

17. A method to impart or modify odor notes of the lily of the valley and citrus types of a consumer product which comprises including in the product a perfuming ingredient comprising the compound (I) of claim 2.

18. A method to impart or modify odor notes of the lily of the valley and citrus types of a consumer product which comprises including in the product a perfuming ingredient comprising the compound (I) of claim 3.

19. A method to impart or modify odor notes of the lily of the valley and citrus types of a consumer product which comprises including in the product a perfuming ingredient comprising the compound (I) of claim 4.

20. A method to impart or modify odor notes of the lily of the valley and citrus types of a consumer product which comprises including in the product a perfuming ingredient comprising the compound (I) of claim 7.

* * * * *